United States Patent
Samaritani et al.

(12) 
(10) Patent No.: US 6,706,681 B1
(45) Date of Patent: Mar. 16, 2004

(54) HCG LIQUID FORMULATIONS

(75) Inventors: Fabrizio Samaritani, Rome (IT); Patrizia Natale, Rome (IT)

(73) Assignee: Applied Research System ARS Holding N.V., Antilles (NL)

( * ) Notice: Subject to any disclaimer, the term of this patent is extended or adjusted under 35 U.S.C. 154(b) by 0 days.

(21) Appl. No.: 08/913,748

(22) PCT Filed: Mar. 21, 1997

(86) PCT No.: PCT/EP95/01055

§ 371 (c)(1), (2), (4) Date: Nov. 21, 1998

(87) PCT Pub. No.: WO96/29095

PCT Pub. Date: Sep. 26, 1996

(51) Int. Cl.$^7$ ................................................ A61K 31/00
(52) U.S. Cl. ................................ 514/2; 514/8; 514/12; 530/395; 530/397; 530/398
(58) Field of Search ................................ 530/395, 397, 530/398; 514/2, 8, 12

(56) References Cited

FOREIGN PATENT DOCUMENTS

| EP | 0448146 | 9/1991 |
|---|---|---|
| EP | 0597101 | 5/1994 |
| WO | 8904177 | 5/1989 |
| WO | 9311788 | * 6/1993 |

* cited by examiner

*Primary Examiner*—James H. Reamer
(74) *Attorney, Agent, or Firm*—Dickstein, Shapiro, Morin & Oshinsky, LLP.

(57) ABSTRACT

The invention refers to liquid pharmaceutical compositions containing hCG stabilised with a polyalcohol or a non-reducing sugar. Preferably, the compositions are stabilised with mannitol.

In the preferred embodiments such compositions are aqueous solutions in a phosphate buffer at pH 7.

Such compositions are ready to be injected and, therefore, the step of reconstitution of the lyophilised powder is avoided, thus simplifying the way of use.

16 Claims, No Drawings

HCG LIQUID FORMULATIONS

The present invention relates to gonadotropin containing liquid pharmaceutical compositions. More precisely, it concerns liquid formulations of hCG (human Chorionic Gonadotropin) stablised with a polyalcohol or a non-reducing sugar.

It is known that highly purified proteins easily undergo degradation, even due to the contact with atmospheric agents. This characteristic is even more evident for proteins produced by recombinant DNA techniques.

Such proteins are usually stabilised with saccharides, such as lactose, or with mannitol, or else with proteins or aminoacids, such as albumin and glycin.

The injectable stabilised formulations of gonadotropins are obtained with a process which includes always a step of lyophilisation to obtain a dry powder; in such a way the stabilised formulations are able to maintain a longer cycle life, even if stored at room temperature.

WO 93/11788 describes lyophilised gonadotropin-containing pharmaceutical compositions stabilised with sucrose, alone or in combination with other stabilising agents. In said patent application it is shown that the stability provided to the lyophilised compositions under study by sucrose was better than that provided by lactose or mannitol.

No liquid stabilised formulations of gonadotropins have been described until now. It is highly desirable to obtain such liquid formulations so as to have the compositions ready to be injected and to avoid the reconstitution of the lyophilised powder, thus simplifying the way of use.

We have surprisingly found that it is possible to obtain such liquid stabilised formulations.

The main object of the present invention is to provide a liquid pharmaceutical composition containing hCG stabilised with a polyalcohol or a non-reducing sugar. Preferably the polyalcohol is mannitol and the non-reducing sugar is sucrose. More preferably the liquid formulations of the invention are stabilised with mannitol.

The solution is preferably a buffered aqueous solution and the buffer according to the invention is selected from the group consisting of phosphate, acetate or succinate buffer. The preferred buffer is phosphate and the pH is preferably 7.00.

The hCG is preferably recombinant and can be prepared, for example, by expression in CHO (Chinese Hamster Ovary) cells, transformed with the corresponding DNA, according to the technique described in European Patent 160699.

A further object of the present invention is to provide a process for the preparation of said liquid pharmaceutical composition comprising diluting a hCG bulk solution in a buffer solution containing the excipients.

Still another object of the present invention is to provide a form of presentation of said liquid pharmaceutical composition comprising such formulation hermetically closed in a sterile condition in a container suitable for the storage before the use.

In order to optimise the stability of the hCG formulations of the invention, a series of preliminary experiments have been carried out with different buffers at various pH, ionic strength, dielectric constant and concentration of rec-hCG.

In order to evaluate the effect of pH and of the buffer, 0.01 M solutions of phosphate, succinate or acetate buffers were prepared with water for injection. The pH was adjusted to 6.0, 7.0 or 8.0 with NaOH 1 M. The bulk solution of rec-hCG was added to the buffer systems to obtain solutions at 5,000 IU/ml. The solutions were then filtered and poured into 3 ml glass vials. The composition of the formulations thus prepared is reported in Table 1. The accelerated stability of these formulations has been studied, so that the stability of the same can be foreseen when they are stored in containers at room temperature, through the extrapolation of the data at higher temperatures. In this case, the samples were stored at 40° and 50° C. and the stability of rec-hCG was checked by determining its purity by HPSEC analyses according to the following standard conditions:

| | |
|---|---|
| Phase A | 0.1M phosphate pH 6.7 + 0.1M Na$_2$SO$_4$ |
| Isocratic conditions | 100% phase A |
| Column | TSK G 2000 SWXL |
| Flow Rate | 0.5 ml/min |
| UV Detector | 214 nm |
| Injection Volume | 20 µl (10,000 IU strength) |
| | 40 µl (5,000 IU strength) |

Table 3 reports the percentage of rec-hCG monomer peak determined by HPSEC. The results show that the solutions at pH 6.0 and 8.0 are less stable in comparison with the solutions at pH 7.0 and that no remarkable stability differences were observed among the buffers.

The effect of the ionic strength was evaluated on rec-hCG 5,000 IU/ml solutions, prepared with phosphate and succinate buffers 0.01M at pH 7.0, adjusted with NaCl to the following values of osmolality: 150, 300 and 400 mOsm. The composition of the formulations is reported in Table 2. The samples were stored at 4°, 25°, 40° and 50° C. and tested for the stability of rec-hCG by HPSEC. The results, reported in table 4, show that the increase of ionic strength negatively affects the stability of rec-hCG.

The effect of the dielectric constant was evaluated on 5,000 IU/ml solutions of rec-hCG, prepared with phosphate and succinate buffers 0.01 M at pH 7, containing 5, 10 and 15% propylene glycol. The composition of the formulations is reported on Table 2. The samples were stored at 4°, 25°, 40° and 50° C. and tested for the stability of rec-hCG by HPSEC. The results, reported in Table 4. show that increasing the percentage of propylene glycol negatively affects the stability of rec-hCG.

In order to evaluate the effect of the rec-hCG concentration, the stability at 50° C. of the solutions in phosphate buffer 0.01 M at pH 7.0, containing respectively 2,500, 5,000, 7,500 and 10,000 IU/ml of rec-hCG was monitored by HPSEC for 2 weeks. The results reported in Table 5 showed that the stability was higher for the more concentrated solutions.

In order to compare the effects of various stabilisers and/or excipients on the stability of rec-hCG, six liquid formulations, in phosphate buffer 0.01 M at pH 7.0 containing 10,000 IU/ml rec-hCG were prepared, as a first step. Sucrose, glycine, glucose, mannitol, lactose and NaCl were used, as stabilisers/excipient. The composition of the formulations is reported in Table 6. These formulations were submitted to the stability tests by storing samples at 4°, 25°, 40° and 50° C. and tested by a Bioassay and HPSEC. Subsequently, based on the results of said first step, four lots of two selected liquid formulations were prepared, using as stabilisers sucrose and mannitol. Table 7 reports the composition of such formulations.

The Bioassay has been carried out in accordance with the European Pharmacopoeia Monograph.

In Table 8, the HPSEC stability data are reported and in Table 9, the values of bioactivity are reported. The results showed the following:

1. the bioactivity of the formulations containing glucose and lactose remarkably decreased at 50° C. after 1 week storage. Also monomer peak was lower compared to that measured in the other formulations.

2. in the presence of glycine and NaCl, a more evident decrease of bioactivity and of purity was measured in comparison to the formulations containing sucrose and mannitol. Also in this case the decrease of the percentage of the rec-hCG monomer peak, was not due to the formation of aggregates forms, but to the increase of free subunits.

Tables 10 and 11 report the purity determined by HPSEC for the 5,000 and 10,000 IU strength respectively. Data show that even after three weeks at 50° C. the purity is higher in the formulations containing mannitol compared to the formulations containing sucrose. Tables 12 and 13 report the purity of the ax subunit determined by reverse phase HPLC after 1 week storage at 50° C. for the sucrose and mannitol formulations. The data confirm the better stability of the formulation containing mannitol in comparison to that containing sucrose.

Reverse Phase HPLC analyses have been performed with the following standard conditions:

| Phase A | 1 ml TFA in 1 liter of bidistilled water | | |
|---|---|---|---|
| Phase B | 0.79 ml TFA in 1 liter of acetonitrile | | |
| Gradient conditions | time | A% | B % |
| | 0 | 85 | 15 |
| | 20' | 60 | 40 |
| | 21' | 20 | 80 |
| | 22' | 85 | 15 |
| Column | Aquapore RP 300 25 cm | | |
| Column temperature | 40° C. | | |
| Flow Rate | 1 ml/min | | |
| UV detector | 214 nm | | |
| Injection volume | 10 $\mu$l | | |

In the Tables 14 and 15, the results of the bioactivity assay are reported. No appreciable bioactivity decrease was observed after 24 weeks at 4° and 25° C. in the mannitol formulation.

According to the present invention, the liquid pharmaceutical compositions contain from 1,000 to 40,000 IU/ml, preferably 10,000 IU/ml, of hCG and from 10 to 180 mg/l, preferably 54.6 mg/l, of mannitol in a 0.01 M buffer solution.

EXAMPLES OF PHARMACEUTICAL MANUFACTURING

Materials: Phosphoric acid 85% RPE ACS (Carlo Erba); Mannitol DAB, Ph Eur BP, FU, USP, FCC, E421 (Merck), NaOH 1 M (Merck), water for injections.

The primary container for the formulated vials consists of: 3 ml glass vials (DIN 2R) (borosilicate glass type I), Rubber closures (Pharmagummi W1816 V50), Aluminium rings and flip off caps (Pharma Metal GmbH).

Preparation of Rec-hCG Solution Containing Mannitol

The phosphoric acid (0.98 g) is added to the water for injections (600 ml). If necessary, the pH is adjusted to 7.0 with NaOH 1 M. Mannitol (54.6 g) is added to the phosphoric acid solution and the pH is again checked and, if necessary, adjusted to 7.00∓0.2 with NaOH 1 M or with phosphoric acid diluted 1:5. The rec-hCG bulk (10 MIU or 20 MIU, if the final desired strenght is 5,000 or 10,000 IU respectively) is then added to the excipient solution and the pH is again checked and, if necessary, adjusted to 7.00∓0.2 with NaOH 1 M or with phosphoric acid diluted 1:5.

The solution is brought to 1 liter with water for injections. Such solution is then filtered through a 0.22 $\mu$m Millipak 20 filter under a pressure not higher than 1.5 atm, under laminar flow, collecting the solution intoa flask and stirring gently for about 1 minute.

The vials are then filled up with 0.5 ml of the rec-hCG solution.

TABLE 1

COMPOSITION OF r-hCG SOLUTIONS
pH/buffer effect

| | Amount/ml |
|---|---|
| Acetate buffer solution | |
| r-hCG bulk | 5000 IU |
| Acetic acid glacial | 0.6 mg |
| NaOH 1M | q.s. to pH 6.0, 7.0, 8.0 |
| Succinate buffer solution | |
| r-hCG bulk | 5000 IU |
| Succinic acid | 1.18 mg |
| NaOH 1M | q.s. to pH 6.0, 7.0, 8.0 |
| Phosphate buffer solution | |
| r-hCG bulk | 5000 IU |
| Phosphoric acid 85% | 0.98 mg |
| NaOH 1M | q.s. to pH 6.0, 7.0, 8.0 |

Filling volume: 1 ml

TABLE 2

COMPOSITION OF r-hCG SOLUTIONS
Ionic strength/dielectric constant

| Lot | r-hCG | NaCl | Prop. glyc. | Phosp. buffer 0.01 pH 7.0 | Succinate buffer 0.01M pH 7.0 |
|---|---|---|---|---|---|
| Fos/7.0/PG 5 | 5000 IU/ml | — | 50 mg/ml | q.s. to 1 ml | — |
| Fos/7.0/PG 10 | 5000 IU/ml | — | 100 mg/ml | q.s. to 1 ml | — |
| Fos/7.0/PG 15 | 5000 IU/ml | — | 150 mg/ml | q.s. to 1 ml | — |
| Suc/7.0/PG 5 | 5000 IU/ml | — | 50 mg/ml | — | q.s. to 1 ml |

TABLE 2-continued

| | | | | | |
|---|---|---|---|---|---|
| Suc/7.0/PG 10 | 5000 IU/ml | — | 100 mg/ml | — | q.s. to 1 ml |
| Suc/7.0/PG 15 | 5000 IU/ml | — | 150 mg/ml | — | q.s. to 1 ml |

Filling volume: 1 ml
FOS = Phosphate buffer
SUC = Succinate buffer
7.0 = pH 7.0
PG 5 = propylene glycol 5%
PG 10 = propylene glycol 10%
PG 15 = propylene glycol 15%

| Lot | r-hCG | NaCl | Prop. glyc. | Phosp. buffer 0.01 pH 7.0 | Succinate buffer 0.01M pH 7.0 |
|---|---|---|---|---|---|
| Fos/7.0/150 | 5000 IU/ml | 4.4 mg/ml | — | q.s. to 1 ml | — |
| Fos/7.0/300 | 5000 IU/ml | 8.8 mg/ml | — | q.s. to 1 ml | — |
| Fos/7.0/400 | 5000 IU/ml | 11.7 mg/ml | — | q.s. to 1 ml | — |
| Suc/7.0/150 | 5000 IU/ml | 4.4 mg/ml | — | — | q.s. to 1 ml |
| Suc/7.0/300 | 5000 IU/ml | 8.8 mg/ml | — | — | q.s. to 1 ml |
| Suc/7.0/400 | 5000 IU/ml | 11.7 mg/ml | — | — | q.s. to 1 ml |

Filling volume: 1 ml
150, 300, 400: osmolarity
FOS = Phosphate buffer
SUC = Succinate buffer
7.0 = pH 7.0

TABLE 3 r-hCG PURITY (%)
HPSEC DATA
pH/Buffer effect

| | | 50° C. | | | 40° C. | |
|---|---|---|---|---|---|---|
| LOT | T = 0 | 1 W | 3 W | 5 W | 3 W | 5 W |
| ACE/6 | 100 | 95.85 | 92.70 | 84.99 | 97.51 | 94.10 |
| ACE/7 | 100 | 96.62 | 93.26 | 88.02 | 97.27 | 94.05 |
| ACE/8 | 100 | 96.51 | 92.70 | 87.10 | 97.45 | 95.12 |
| SUC/6 | 100 | 94.56 | 91.28 | 82.11 | 96.92 | 93.11 |
| SUC/7 | 100 | 95.78 | 94.20 | 88.05 | 96.91 | 93.99 |
| SUC/8 | 100 | 95.36 | 90.12 | 83.00 | 97.61 | 94.02 |
| FOS/6 | 100 | 94.10 | 90.76 | 81.00 | 97.50 | 93.00 |
| FOS/7 | 100 | 96.09 | 93.12 | 86.93 | 96.72 | 93.74 |
| FOS/8 | 100 | 94.21 | 82.52 | 74.96 | 96.77 | 93.55 |

W = week
ACE = acetate buffer
SUC = succinate buffer
FOS = phosphate buffer
6/7/8 = pH 6.0, 7.0, 8.0

TABLE 4 r-hCG PURITY (%)
HPSEC DATA
Ionic strength/dielectric constant

| | | 50° C. | | | 40° C. | | 25° C. | 4° C. |
|---|---|---|---|---|---|---|---|---|
| LOT | T = 0 | 1 W | 2 W | 4 W | 3 W | 6 W | 6 W | 4 W |
| Fos/7.0/PG 5 | 100 | 91.9 | 85.7 | 80.8 | 96.5 | 94.3 | 100 | 100 |
| Fos/7.0/PG 10 | 100 | 91.9 | 81.0 | 77.7 | 93.9 | 93.9 | 100 | 100 |
| Fos/7.0/PG 15 | 100 | 89.2 | 79.3 | 76.2 | 94.4 | 93.8 | 100 | 100 |
| Suc/7.0/PG 5 | 100 | 90.6 | 84.3 | — | 91.7 | — | — | — |
| Suc/7.0/PG 10 | 100 | 88.9 | 81.4 | — | 94.1 | — | — | — |
| Suc/7.0/PG 15 | 100 | 89.3 | 79.9 | — | 93.5 | — | — | — |
| Fos/7.0/150 | 100 | 88.5 | 79.2 | 72.2 | 93.0 | 93.0 | 100 | 100 |
| Fos/7.0/300 | 100 | 80.5 | 75.0 | 67.9 | 93.4 | 92.1 | 100 | 100 |
| Fos/7.0/400 | 100 | 81.5 | 74.8 | 67.4 | 94.6 | 93.8 | 100 | 100 |
| Suc/7.0/150 | 100 | 83.1 | 87.4 | — | 94.3 | — | — | — |

TABLE 4-continued r-hCG PURITY (%)
HPSEC DATA
Ionic strength/dielectric constant

| | | 50° C. | | | 40° C. | | 25° C. | 4° C. |
|---|---|---|---|---|---|---|---|---|
| LOT | T = 0 | 1 W | 2 W | 4 W | 3 W | 6 W | 6 W | 4 W |
| Suc/7.0/300 | 100 | 82.4 | 76.7 | — | 93.9 | — | — | — |
| Suc/7.0/400 | 100 | 81.8 | 74.6 | — | 93.5 | — | — | — |

— = not tested
FOS = Phosphate buffer
SUC = Succinate buffer
7.0 = pH 7.0
PG 5 = propylene glycol 5%
PG 10 = propylene glycol 10%
PG 15 = propylene glycol 15%
150, 300, 400 = osmolarity
W = week

TABLE 5 r-hCG PURITY (%)
HPSEC DATA
concentration effect

| | | 50° C. | |
|---|---|---|---|
| LOT | T = 0 | 1 W | 2 W |
| Fos/2500 | 100 | 87.3 | 84.0 |
| Fos/5000 | 100 | 90.8 | 89.1 |
| Fos/7500 | 100 | 92.9 | 89.8 |
| Fos/10000 | 100 | 92.5 | 90.9 |

Fos/2500: 2,500 IU/ml of r-hCG
Fos/5000: 5,000 IU/ml of r-hCG
Fos/7500: 7,500 IU/ml of r-hCG
Fos/10000: 10,000 IU/ml of r-hCG

TABLE 6

LIQUID FORMULATIONS
Vial composition

| COMPON-ENTS/LOT | r-hCG/SAC | r-hCG/MAN | r-hCG/GLY | r-hCG/GLU | r-hCG/LAT | r-hCG/NaCl |
|---|---|---|---|---|---|---|
| r-hCG IU/ml | 10,000 | 10,000 | 10,000 | 10,000 | 10,000 | 10,000 |
| SUCROSE mg/ml | 102.6 | — | — | — | — | — |
| MANNITOL mg/ml | — | 54.6 | — | — | — | — |
| GLYCINE mg/ml | — | — | 22.52 | — | — | — |
| GLUCOSE mg/ml | — | — | — | 54.6 | — | — |
| LACTOSE mg/ml | — | — | — | — | 102.6 | — |
| NaCl mg/ml | — | — | — | — | — | 9.0 |

Buffer: $H_3PO_4$ 0.01M, pH 7.0
Filling volume: 0.5 ml

TABLE 7

LIQUID FORMULATIONS
Vial composition

| COMPONENT | UNIT | r-hCG/5000/S01 | r-hCG/10000/S01 |
|---|---|---|---|
| r-hCG | IU/ml | 10,000 | 20,000 |
| SUCROSE | mg/ml | 102.6 | 102.6 |
| O. PHOSPHORIC ACID | mg/ml | 0.98 | 0.98 |
| SODIUM HYDROXIDE | | q.s. to pH 7.0 | q.s. to pH 7.0 |

| COMPONENT | UNIT | r-hCG/5000/M01 | r-hCG/1000/M01 |
|---|---|---|---|
| r-hCG | IU/ml | 10,000 | 20,000 |
| MANNITOL | mg/ml | 54.6 | 54.6 |
| O. PHOSPHORIC ACID | mg/ml | 0.98 | 0.98 |
| SODIUM HYDROXIDE | | q.s. to pH 7.0 | q.s. to pH 7.0 |

Filling volume: 0.5 ml

TABLE 8

COMPATIBILITY WITH DIFFERENT EXCIPIENTS
HPSEC stability data: purity (%)

| | | 50° C. | | | 40° C. | | | | 25° C. | | | | 4° C. | |
|---|---|---|---|---|---|---|---|---|---|---|---|---|---|---|
| LOT | T = 0 | 1 W | 2 W | 6 W | 2 W | 4 W | 6 W | 11 W | 4 W | 6 W | 8 W | 11 W | 8 W | 12 W |
| FOS/SAC | 100 | 94.1 | 90.3 | 83.0 | 98.0 | 95.5 | 96.1 | 94.8 | 100 | 100 | 100 | 100 | 100 | 100 |
| FOS/GLY | 100 | 94.2 | 90.4 | 81.5 | 97.5 | 96.3 | 95.5 | 95.5 | 100 | 100 | 100 | 100 | 100 | 100 |
| FOS/GLU | 100 | 85.0 | 74.9 | N.T. | 88.0 | N.T. | N.T. | N.T. | N.T. | N.T. | N.T. | N.T. | N.T. | N.T. |
| FOS/MAN | 100 | 94.0 | 91.7 | 83.5 | 97.9 | 97.1 | 95.8 | 95.4 | N.T. | 100 | 100 | 100 | 100 | 100 |

TABLE 8-continued

COMPATIBILITY WITH DIFFERENT EXCIPIENTS
HPSEC stability data: purity (%)

| | | 50° C. | | | 40° C. | | | | 25° C. | | | | 4° C. | |
|---|---|---|---|---|---|---|---|---|---|---|---|---|---|---|
| LOT | T = 0 | 1 W | 2 W | 6 W | 2 W | 4 W | 6 W | 11 W | 4 W | 6 W | 8 W | 11 W | 8 W | 12 W |
| FOS/LAT | 100 | 88.3 | 71.6 | N.T. | 89.0 | N.T. | N.T. | N.T. | N.T. | N.T. | N.T. | N.T. | N.T. | N.T. |
| FOS/NaCl | 100 | 89.7 | 85.6 | 71.7 | 97.2 | 95.2 | 94.2 | 94.1 | N.T. | 100 | 100 | 98.5 | 100 | 100 |

W = week
Filling volume = 0.5 ml
FOS = Phosphate buffer
SAC = Sucrose, GLY = glycine, GLU = glucose, MAN = mannitol, LAT = lactose
N.T. = not tested

TABLE 9

COMPATIBILITY WITH DIFFERENT EXCIPIENTS
Bioassay data (IU/ml)

| | | 50° C. | | | 40° C. | | | | 25° C. | | 4° C. | |
|---|---|---|---|---|---|---|---|---|---|---|---|---|
| LOT | T = 0 | 1 W | 2 W | 7 W | 2 W | 4 W | 7 W | 10 W | 8 W | 11 W | 8 W | 12 W |
| FOS/SAC | 9473 | 7854 | 8245* | N.V. | 8098 | 10368 | 9126 | 8269 | 8809* | 11222 | 9588 | 8489 |
| FOS/GLY | 7850* | 5642 | 4913 | — | 6421 | 8112 | 6780 | 6635* | — | 7159 | — | 6821* |
| FOS/GLU | 8370 | N.V. | — | — | — | — | — | — | — | — | — | — |
| FOS/MAN | 9498 | 7031 | 7224 | 6321* | 10605 | 13216 | 9374* | 6904 | 7285 | 7941 | 10079 | 8762 |
| FOS/LAT | 7976 | N.V. | — | — | — | — | — | — | — | — | — | — |
| FOS/NaCl | 8486 | 8394 | 6433 | — | 9262 | 10576 | | 7578 | 9151* | 9353* | 8804 | 8377 |

W = week
Filling volume = 0.5 ml
* = one valid assay
N.V. = not valid assay
— = not tested
FOS: Phosphate buffer, SAC = Sucrose, GLY = glycine, GLU = glucose, MAN = mannitol, LAT = lactose

TABLE 10

LIQUID FORMULATION: CONC. 5,000 IU/vial
HPSEC Stability data: purity (%)
Formulation development

| | | 50° C. | | 40° C. |
|---|---|---|---|---|
| LOT | T = 0 | 1 W | 3 W | 3 W |
| HCG/5000/S01 | 100 | 90.0 | 86.3 | 97.2 |
| HCG/5000/M01 | 100 | 89.5 | 88.3 | 97.6 |

W = week
S01 = sucrose
M01 = mannitol

TABLE 11

LIQUID FORMULATION: CONC. 10,000 IU/vial
HP-SEC Stability data: purity (%)
Formulation development

| | | 50° C. | | 40° C. |
|---|---|---|---|---|
| LOT | T = 0 | 1 W | 3 W | 3 W |
| HCG/10000/S01 | 100 | 91.8 | 88.9 | 97.9 |
| HCG/10000/M01 | 100 | 93.4 | 92.1 | 97.2 |

W = week
S01 = sucrose
M01 = mannitol

TABLE 12

LIQUID FORMULATION
α subunit purity by RP-HPLC

| | | 50° C. |
|---|---|---|
| LOT | T = 0 | 1 W |
| HCG/5000/S01 α (%) | 100 | 90.2 |
| HCG/5000/M01 α (%) | 100 | 94.7 |

W = week
S01 = Sucrose
M01 = Mannitol

TABLE 13

LIQUID FORMULATION
α subunit purity by RP-HPLC

| | | 50° C. |
|---|---|---|
| LOT | T = 0 | 1 W |
| HCG/10000/S01 α (%) | 100 | 92.4 |
| HCG/10000/M01 α (%) | 100 | 95.1 |

W = week
S01 = Sucrose
M01 = Mannitol

TABLE 14

LIQUID FORMULATION
Bioassay data (IU/ml)

| | | | 50° C. | | |
|---|---|---|---|---|---|
| LOT | T = 0 | 1 W | 3 W | 4 W | 5 W |
| HCG/5000/S01 | 09194 (7484–11298) | 6427 (4770–8660) | 6757 (5454–8371) | — | NV |
| HCG/5000/M01 | 8548 (6376–11459) | 9249 (7495–11414) | 6977 (5649–8618) | 6207 (4767–8082) | 3219* (1436–5150) |

| | | 40° C. | | |
|---|---|---|---|---|
| LOT | 4 W | 6 W | 10 W | 13 W |
| HCG/5000/S01 | 8632* (6082–12393) | 10102 (7733–13195) | 8192 (6276–10692) | — |
| HCG/5000/M01 | 10203 (7813–13325) | 7959 (6118–10356) | — | 7309 (5932–9005) |

| | | 25° C. | | |
|---|---|---|---|---|
| LOT | T = 0 | 5 W | 13 W | 24 W |
| HCG/5000/S01 | 9194 (7484–11298) | — | — | — |
| HCG/5000/M01 | 8548 (6376–11459) | 6660* (3855–10118) | 8969 (7007–11479) | 8232* (5787–11712) |

| | | 4° C. | |
|---|---|---|---|
| LOT | 5 W | 13 W | 24 W |
| HCG/5000/S01 | 7555 (5904–9667) | — | — |
| HCG/5000/M01 | 8869* (5968–12826) | 10330 (8167–13065) | 9799 (7714–12447) |

W = Week
NV = not valid assay
S01 = Sucrose
M01 = Mannitol
* = one valid assay

TABLE 15

LIQUID FORMULATION: 10,000 IU/VIAL
Bioassay data (IU/ml)

| | | | 50° C. | |
|---|---|---|---|---|
| LOT | T = 0 | 1 W | 2 W | 4 W |
| HCG/10000/S01 | 20273 (15170–27091) | 15531 (11842–20368) | 14971 (11307–19824) | — |
| HCG/10000/M01 | 18919 (14150–25295) | 15880 (12605–20006) | 13495 (9994–18222) | 14855 (11579–19058) |

| | | 40° C. | |
|---|---|---|---|
| LOT | 4 W | 6 W | 13 W |
| HCG/10000/S01 | 22201 (16648–29607) | 14977 (12075–18576) | — |
| HCG/10000/M01 | 19508 (14201–26797) | 14680 (11328–19022) | 14606 (11580–18423) |

| | | | 25° C. | | |
|---|---|---|---|---|---|
| LOT | T = 0 | 5 W | 10 W | 13 W | 24 W |
| HCG/10000/S01 | 20273 (15170–27091) | — | 17812* (11809–26112) | — | — |
| HCG/10000/M01 | 18919 (14150–25295) | 17890 (14467–22122) | 15494 (12638–18996) | 16419 (12890–20915) | 18991 (15311–23556) |

TABLE 15-continued

| | 4° C. | | |
|---|---|---|---|
| LOT | 5 W | 13 W | 24 W |
| HCG/10000/S01 | 21616 (17596–26555) | — | — |
| HCG/10000/M01 | 20666 (17390–24559) | 17096 (13503–21646) | 19553 (14494–26377) |

W = Week
NV = not valid assay
S01 = Sucrose
M01 = Mannitol
*= one valid assay

What is claimed is:

1. A stable, liquid pharmaceutical composition comprising recombinant human Chorionic Gonadotropin and a stabilizing amount of mannitol.

2. A liquid pharmaceutical composition according to claim 1, wherein the solution is a buffered aqueous solution.

3. A liquid pharmaceutical composition according to claim 2, wherein the buffer solution is selected from the group consisting of acetate, succinate and phosphate buffer.

4. A liquid pharmaceutical composition according to claim 3, wherein the buffer is phosphate buffer.

5. A liquid pharmaceutical according to claim 2, wherein the buffer solution is at pH 7.0.

6. A liquid pharmaceutical composition according to claim 2, wherein the buffer solution is 0.01 M.

7. A liquid pharmaceutical composition according to claim 1, comprising from 1,000 to 40,000 IU/ml of rhCG and from 10 to 180 mg/l of mannitol in a 0.01 M phosphate buffer at pH 7.0.

8. A process for the preparation of a liquid pharmaceutical composition according to claim 1, comprising diluting a rhCG bulk solution in a buffer solution containing exipients.

9. The liquid pharmaceutical composition of claim 1 hermetically closed in a sterile condition in a container suitable for the storage before use.

10. A liquid pharmaceutical composition according to claim 3, wherein the buffer solution is at pH 7.0.

11. A liquid pharmaceutical composition according to claim 4, wherein the buffer solution is at pH 7.0.

12. A liquid pharmaceutical composition according to claim 3, wherein the buffer solution is 0.01 M.

13. A liquid pharmaceutical composition according to claim 4, wherein the buffer solution is 0.01 M.

14. A liquid pharmaceutical composition according to claim 5, wherein the buffer solution is 0.01 M.

15. A liquid pharmaceutical composition according to claim 10, wherein the buffer solution is 0.01 M.

16. A liquid pharmaceutical composition according to claim 11, wherein the buffer solution is 0.01 M.

* * * * *

UNITED STATES PATENT AND TRADEMARK OFFICE
CERTIFICATE OF CORRECTION

PATENT NO. : 6,706,681 B1 Page 1 of 1
DATED : March 16, 2004
INVENTOR(S) : Fabrizio Samaritani et al.

It is certified that error appears in the above-identified patent and that said Letters Patent is hereby corrected as shown below:

Title page,
Item [22], PCT Filed, "Mar. 21, 1997", should read -- Mar. 21, 1995 --.

Signed and Sealed this

Twenty-third Day of November, 2004

JON W. DUDAS
*Director of the United States Patent and Trademark Office*